United States Patent
Kolen et al.

[19]

[11] Patent Number: 5,980,561
[45] Date of Patent: *Nov. 9, 1999

[54] APPLYING THERMAL THERAPY TO LIVING TISSUE

[76] Inventors: Paul T. Kolen, 139 Fourth St., Encinitas, Calif. 92024; Thomas D. Ford, 10405 Orozco St., San Diego, Calif. 94124

[ * ] Notice: This patent is subject to a terminal disclaimer.

[21] Appl. No.: 08/860,307

[22] PCT Filed: Mar. 1, 1995

[86] PCT No.: PCT/US96/02824

§ 371 Date: Dec. 31, 1997

§ 102(e) Date: Dec. 31, 1997

[87] PCT Pub. No.: WO96/26693

PCT Pub. Date: Sep. 6, 1996

Related U.S. Application Data

[63] Continuation-in-part of application No. 08/450,641, May 25, 1995, Pat. No. 5,865,841.

[30] Foreign Application Priority Data

Mar. 1, 1995 [IE] Ireland .................................. S950163

[51] Int. Cl.⁶ .................................................. A61F 7/00
[52] U.S. Cl. .......................................... 607/104; 607/114
[58] Field of Search .................................. 607/104, 107, 607/108–112, 114; 236/12.12, 12.1, 12.11

[56] References Cited

U.S. PATENT DOCUMENTS

| | | | |
|---|---|---|---|
| 2,726,658 | 12/1955 | Chessey | 128/400 |
| 3,744,555 | 7/1973 | Fletcher et al. | 165/46 |
| 3,871,381 | 3/1975 | Roslonski | 128/400 |
| 4,026,299 | 5/1977 | Sauder | 128/400 |
| 4,149,529 | 4/1979 | Copeland et al. | 128/24.1 |
| 4,184,537 | 1/1980 | Sauder | 165/46 |
| 4,243,041 | 1/1981 | Paul | 128/402 |
| 4,523,594 | 6/1985 | Kuznetz | 128/402 |
| 4,691,762 | 9/1987 | Elkins et al. | 165/46 |
| 4,821,354 | 4/1989 | Little | 5/422 |
| 4,964,402 | 10/1990 | Grim et al. . | |
| 5,050,062 | 9/1991 | Hass | 236/12.12 |
| 5,051,562 | 9/1991 | Bailey et al. | 219/506 |
| 5,167,655 | 12/1992 | McCoy | 604/396 |
| 5,241,951 | 9/1993 | Mason et al. | 607/104 |
| 5,330,519 | 7/1994 | Mason et al. | 607/104 |
| 5,466,251 | 11/1995 | Brunson et al. | 607/112 |
| 5,476,489 | 12/1995 | Koewler | 607/104 |

OTHER PUBLICATIONS

Burke/Neutech Medical Systems, "The Thermal Therapy People," sales brochure.

Seabrook Medical System, "Cool–Aid Single–Patient Use Cold Therapy System," brochure, 1994.

Breg, Inc., "Polar Care Cold Therapy," brochure.

Seabrook Medical System, Inc., "Electri–Cool Localized Cold Therapy System," brochure, 1991.

Danniger Medical Technology, Inc., "Thermal–Max Hot and Cold Thermal Therapy," brochure.

Burke/Weutech, Inc., "The Standard in Thermal Therapy," brochure.

*Primary Examiner*—Robert L. Nasser
*Attorney, Agent, or Firm*—Fish & Richardson P.C.

[57] ABSTRACT

A thermal therapy device for applying temperature controlled therapy to a therapy site on a mammalian body, comprising: a therapy pad for applying a selected therapy temperature to the therapy site; a recirculating fluid loop comprising a fluid channel defined by the therapy pad; a pump for circulating fluid through the recirculating fluid loop; a thermal reservoir; a heat exchanger coupling the thermal reservoir with the recirculating fluid loop; and a control mechanism coupled to the heat exchanger for enabling adjustable control of therapy temperature. The heat exchanger selectively mixes fluid recirculating in the fluid loop with fluid from the thermal reservoir in an adjustable mixing ratio to achieve the selected therapy temperature at the therapy site.

38 Claims, 8 Drawing Sheets

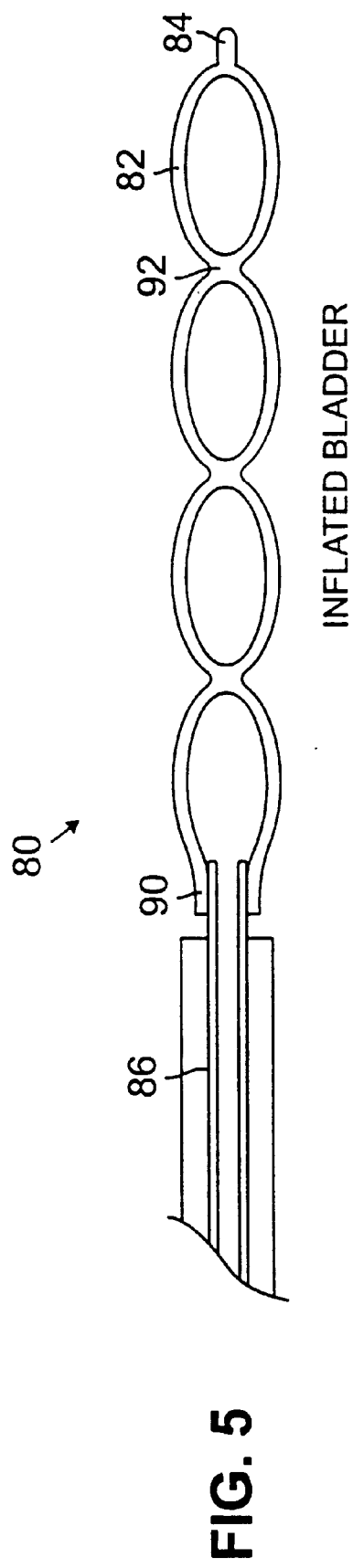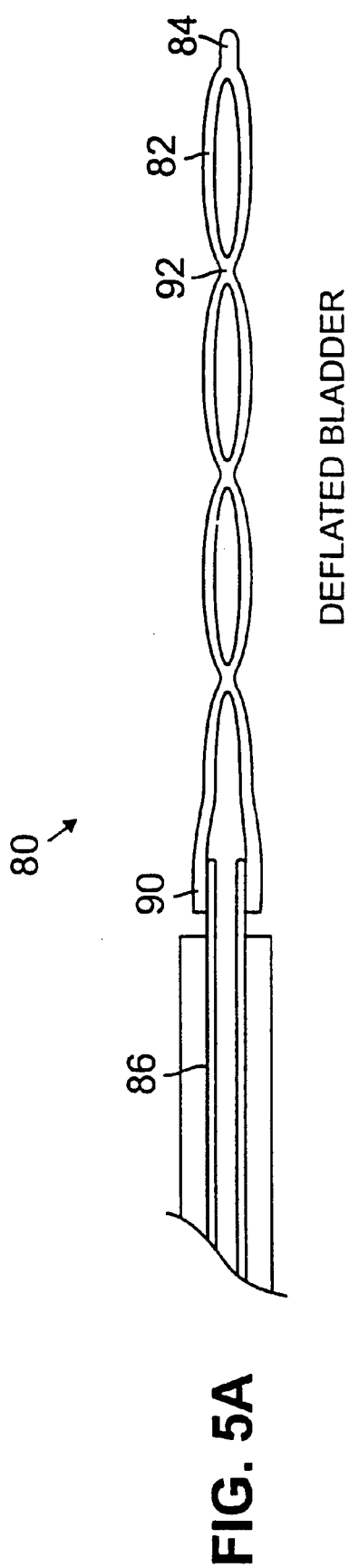

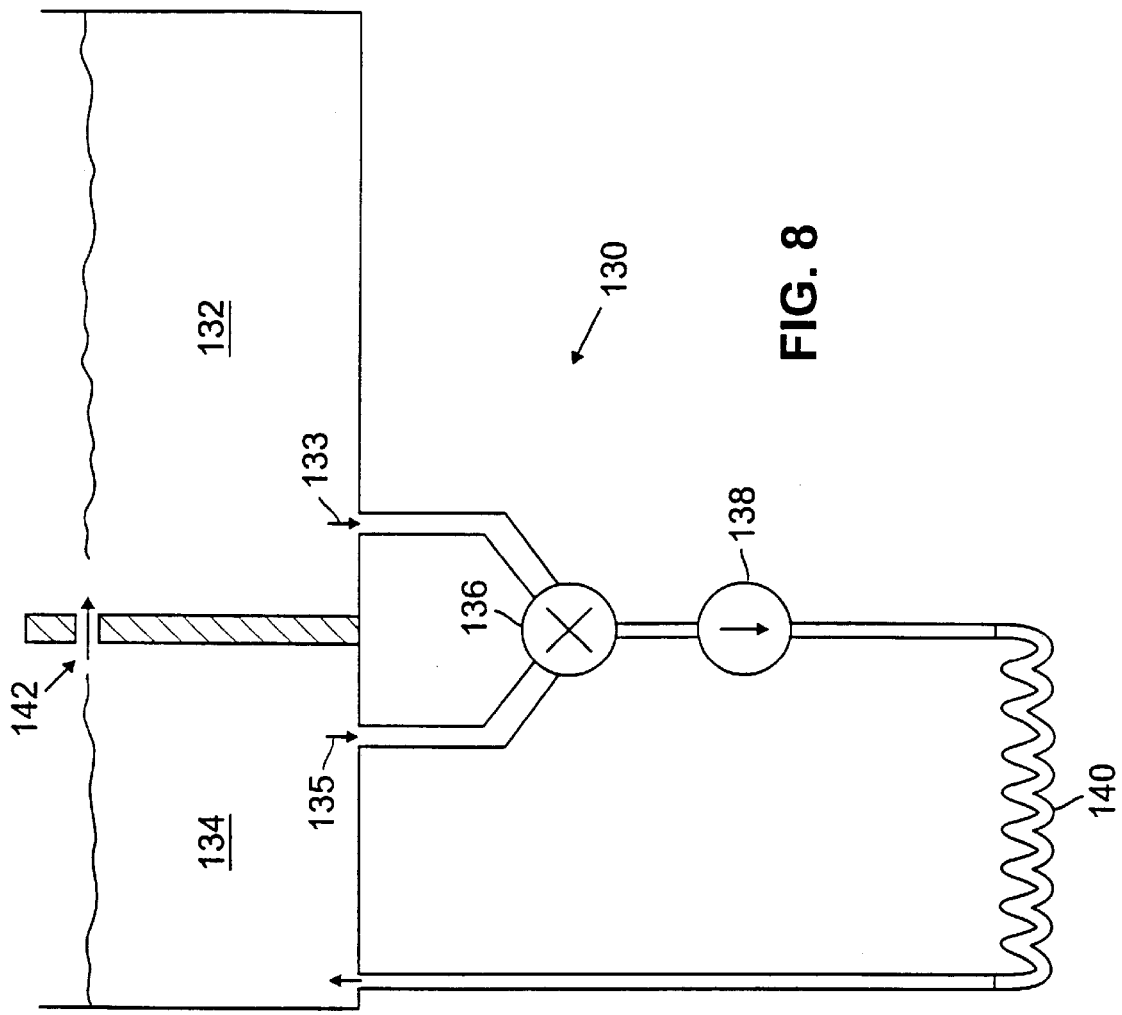

APPLYING THERMAL THERAPY TO LIVING TISSUE

This is a continuation-in-part of U.S. application Ser. No. 08/450,641, filed May 25, 1995, now U.S. Pat. No. 5,865,841.

BACKGROUND OF THE INVENTION

This invention relates to devices and methods for applying thermal therapy to living tissue.

Thermal therapy involves the application of heat or cold to tissue to heal and rehabilitate injuries, such as, bruises, sprains, or other trauma to bone, muscle, ligaments, tendons, and skin. Cold therapy can be used to reduce swelling, reduce pain and promote healing of injured tissue. Heat therapy can be used to loosen joint tissue, such as, ligaments and tendons, to increase range of motion, e.g., before strenuous activity. Thermal therapy can be used after surgery to reduce pain and swelling and promote healing. Thermal therapy can also be used as part of an orthopedic therapy program, a sports medicine program, and to heal and rehabilitate animals, such as, thoroughbred race horses.

Common thermal therapy methods, e.g., application of an ice bag or a hot water bottle, are difficult to hold in place, are statically applied, cause uneven cooling or heating across the treatment site, and do not allow the cooling or heating temperature to be readily controlled.

A number of devices have been proposed for applying cold therapy to living tissue, with or without pressure. One device that has been developed for cooling a human knee includes a large cooler that contains chilled water which is circulated through a tube and into a cooling pad. The cooling pad is applied to a desired therapy site and held in place by a strap. The cooling rate is adjusted by increasing or decreasing the flow resistance through the tube leading to the cooling pad. Miller U.S. Pat. No. 2,531,074 describes a device which includes a flexible, multi-chamber thermal pad into which heated or cooled water is alternately injected at high and low pressures to provide temperature-controlled message therapy. Chessey U.S. Pat. No. 2,726,658 describes a system in which a coolant is pumped directly from a thermostatically-controlled refrigeration system into a cooling pad. Grossan U.S. Pat. No. 3,993,053 describes a massaging pad that includes a set of elastic tubing coils through which temperature controlled fluid is pulsed at high and low pressures to achieve a massaging effect. Copeland U.S. Pat. No. 4,149,529 describes a system that delivers heated or cooled liquid into a dry appliance for performing temperature and intermittent compression treatment; the system also provides a thermal therapy bath treatment.

SUMMARY OF THE INVENTION

In one aspect, the invention features a thermal therapy device for applying temperature controlled therapy to a therapy site on a mammalian body, comprising: a therapy pad for applying a selected therapy temperature to the therapy site; a recirculating fluid loop comprising a fluid channel defined by the therapy pad; a pump for circulating fluid through the recirculating fluid loop; a thermal reservoir; a heat exchanger coupling the thermal reservoir with the recirculating fluid loop; and a control mechanism coupled to the heat exchanger for enabling adjustable control of therapy temperature.

In another aspect, the invention features a thermal therapy device for applying temperature-controlled therapy to a therapy site on a mammalian body, comprising: a therapy pad for applying a selected therapy temperature to the therapy site; a recirculating fluid loop comprising a fluid channel defined by the therapy pad; a thermal reservoir; and a heat exchanger coupling the thermal reservoir with the recirculating fluid loop, the heat exchanger being constructed and arranged to selectively mix fluid recirculating in the fluid loop with fluid from the thermal reservoir in an adjustable mixing ratio to achieve the selected therapy temperature at the therapy site.

Embodiments of the invention may include one or more of the following features. The heat exchanger preferably comprises means for delivering a predetermined volume of fluid from the thermal reservoir into the recirculating fluid loop. The therapy pad preferably includes a flexible surface, and the control mechanism is preferably coupled to the pump for enabling adjustable control of fluid pressure in the therapy pad. The control mechanism is preferably adapted to vary pressure of recirculating fluid within the therapy pad in a manner to apply tactile stimulation to a therapy site by increasing and decreasing fluid pressure in the therapy pad. The control mechanism preferably comprises an alarm adapted to actuate whenever the thermal reservoir lacks thermal capacity to maintain a predetermined therapy temperature.

In some embodiments, the recirculating fluid loop comprises a first temperature sensor for monitoring therapy temperature. In these embodiments, the control mechanism preferably comprises control electronics for the heat exchanger. The control electronics are preferably coupled to the first temperature sensor, user-operated controls and a display for manual selection and visual confirmation of therapy temperature. The control electronics also preferably comprise an associated operating program and means for programming, storing and retrieving a therapy temperature-time profile for implementing therapy temperature control. The control electronics further preferably comprise means for determining a time-varying therapy temperature specified in the therapy temperature-time profile in real time for implementing therapy temperature control. The electronics may comprise means for comparing time-varying therapy temperature applied at the therapy site to a temperature specified in the therapy temperature-time profile in real time for implementing closed-loop therapy temperature control. The control electronics may also comprise an alarm for warning a user when the thermal reservoir lacks thermal capacity to maintain therapy temperature. The alarm preferably comprises a second temperature sensor connected to the control electronics for monitoring temperature in the recirculating fluid loop of fluid exiting the therapy pad, the first temperature sensor monitoring temperature in the recirculating fluid loop of fluid entering the therapy pad, the control electronics monitoring the first temperature sensor and the second temperature sensor and producing a signal when temperatures detected by the first temperature sensor and the second temperature sensor indicate that the thermal reservoir has insufficient thermal capacity to maintain a selected therapy temperature within a preset tolerance value.

The heat exchanger preferably comprises a second thermal reservoir. The heat exchanger also preferably comprises a valve for selectively mixing fluid from the first thermal reservoir with fluid from the second thermal reservoir according to a prescribed mixing ratio and for introducing mixed fluid to the pump for circulation in the recirculating fluid loop. In some embodiments, the control mechanism comprises a knob for manually adjusting the valve to achieve the prescribed mixing ratio.

In some embodiments, the second thermal reservoir comprises an air/water separator. In other embodiments, the heat exchanger comprises a second pump for delivering fluid from the first thermal reservoir to the second reservoir, and further comprises an overflow fluid path for returning excess fluid in the second thermal reservoir to the first thermal reservoir. The control mechanism preferably selectively adjusts the second pump to achieve a prescribed fluid temperature in the second thermal reservoir.

There is a need for a cost-effective thermal therapy device for applying cold or heat therapy to a human or mammalian body that is small enough to be easily transported and used in a wide variety of locations, adaptable to many different mammalian body forms and potential therapy sites, capable of providing controlled temperature therapy at a preset temperature or by a preprogrammed temperature profile, capable of monitoring the therapy temperature directly at the therapy site, and capable of providing tactile stimulation to the therapy site to alleviate the problems of static thermal therapy and enhance the beneficial effects of thermal therapy. The present invention fulfills these needs, and further provides related advantages.

Other features and advantages of the invention will become apparent from the following description of presently preferred embodiments, and from the claims.

BRIEF DESCRIPTION OF THE DRAWINGS

FIGS. 5 and 5A are cross-sectional views of the treatment pad of FIG. 4 shown in inflated condition and deflated condition, respectively.

FIG. 8 is a schematic diagram of another alternative thermal therapy device.

DESCRIPTION OF THE PREFERRED EMBODIMENTS

Figure 1:
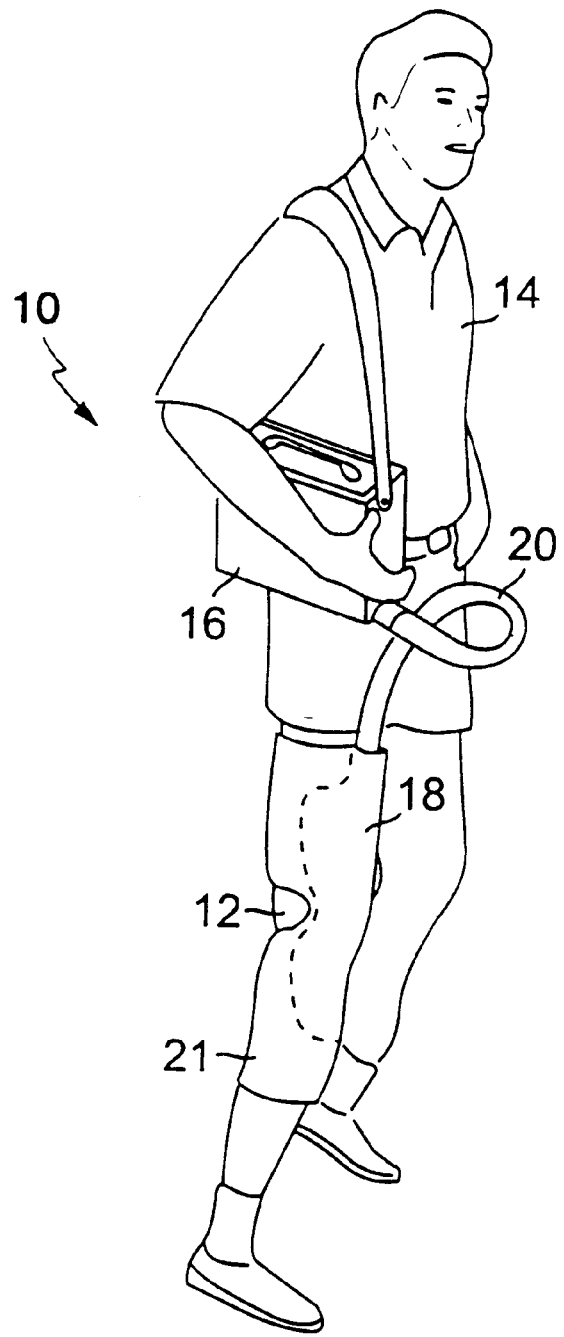
FIG. 1 is a diagrammatic view of a thermal therapy device of the invention for applying thermal therapy to the knee of a person.

Referring to FIG. 1, a thermal therapy device 10 applies temperature-controlled thermal therapy to the knee 12 of a person 14. Thermal therapy device 10 includes a portable reservoir 16 that is connected to a thermal therapy treatment pad 18 by a thermally insulated supply and return assembly 20. As described in detail below, thermal therapy device 10 uniformly heats or cools the person's knee according to a predetermined temperature schedule, and can be programmed to stimulate the patient's knee by controllably varying the inflation pressure inside treatment pad 18. A wrap 21, which is made of, e.g., neoprene rubber, is shaped to snugly hold treatment pad 18 in place at the therapy site, while allowing the treatment pad to expand and contract during tactile stimulation of the person's knee. Wrap 21 is held in place by VELCRO®, i.e. hook-and-loop type, fasteners that allow the wrap to be selectively adjusted to fit firmly, evenly and comfortably in place at the therapy site.

Figure 2:
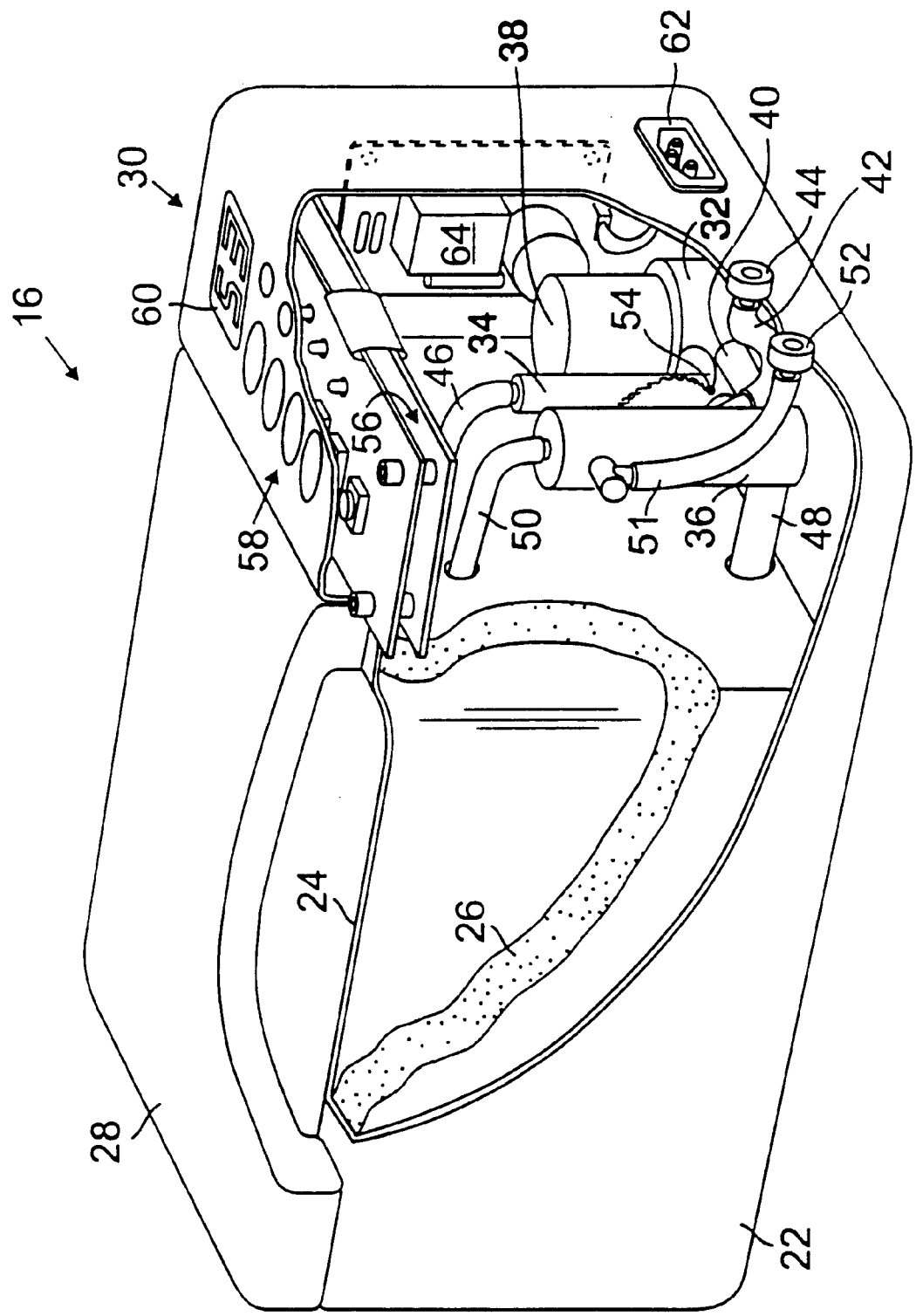
FIG. 2 is a perspective view, partially broken away, of a reservoir housing for a thermal therapy device of the invention.

Referring to FIG. 2, in one embodiment, portable reservoir 16 includes a protective outer case 22 and an inner, leak-proof thermal reservoir 24. Reservoir 24 is thermally insulated by a thermal lining 26, which fills the space between the outer walls of reservoir 24 and the inner wall of outer case 22. A thermally insulated lid 28 opens to provide access to reservoir 24. Lid 28 includes a seal (not shown) sized and constructed to form a fluid-tight seal between lid 28 and the top opening of reservoir 24 when the lid is closed, to prevent fluid from leaking during use.

A fluid control system 30 is contained within the housing, in a compartment space provided between the thermal reservoir and the outer casing. A heat exchanger 31, within the fluid control system, includes a pump 32, a single pole, double-throw priming valve 34, and an air/water separator 36. (In some embodiments, a solenoid valve may replace the single pole, double-throw priming valve.) Pump 32 includes an input 40 and an output 42, and is powered by a motor 38. Pump input 40 is connected to the output of priming valve 34, and pump output 42 is connected to a quick-disconnect outlet 44, through which fluid flows from the pump to the treatment pad. An input 46 of priming valve 34 is connected to thermal reservoir 24, and an input 48 of the priming valve is connected to an output of air/water separator 36. An overflow tube 50 provides a fluid path between the air/water separator and thermal reservoir 24. Air/water separator 36 receives fluid from the treatment pad through tubing 51 from a quick-disconnect inlet 52. The temperature of the fluid that is supplied to the treatment pad is monitored by thermistors 54 placed in the fluid paths of the supply and return lines of supply and return assembly 20.

Reservoir 24 accommodates crushed ice, ice cubes and pre-formed freezable cold sources, such as, those commonly used in portable coolers. The reservoir is easily recharged with additional ice if needed during use, without requiring the person to remove the pad from the therapy site. For heat therapy, hot water can be introduced into the reservoir, or the reservoir fluid can be controllably heated using an immersion heater.

The temperature of the fluid supplied to the treatment pad is controlled by a microprocessor-based controller 56 (control electronics). Based on the therapy temperature measured by thermistors 54, controller 56 produces an audible alarm signal when the cold or heat source in the reservoir is exhausted and the desired therapy temperature cannot be maintained within preset tolerances; an alarm also sounds if the unit detects a restricted flow in the circulation system. Controller 56 incorporates a non-volatile electronic memory for storing, recalling and implementing one or more preprogrammed or user-defined therapy temperature time profiles. Input keys 58 are used to program the desired temperature profile into controller memory. The monitored temperature is shown on a digital display 60. Display 60 may also indicate the amount of therapy time remaining. Electrical power is supplied to fluid control system 30 from a conventional wall outlet, through power connector 62, to switching power electronics 64.

Figure 2A:
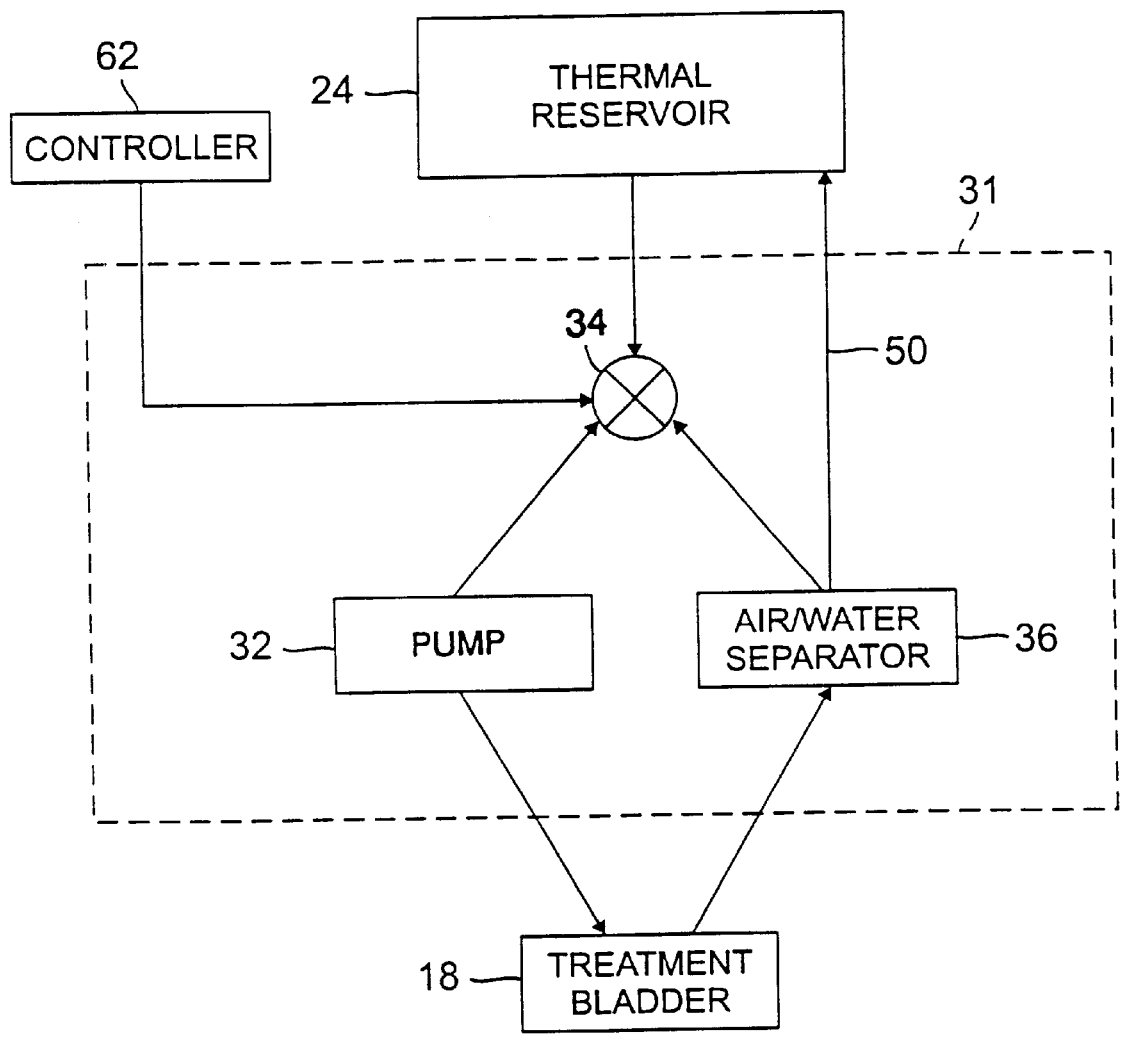
FIG. 2A is a schematic diagram of the thermal therapy device of FIG. 1, including a thermal reservoir, a heat exchanger, and a treatment pad.

As shown in FIG. 2A, heat exchanger 31 controls the temperature of treatment pad 18 by mixing a controlled amount of fluid from thermal reservoir 24 with recirculated fluid returning from the treatment pad through air/water separator 36. By using the real-time temperature information generated by thermistors 54, controller 56 adjusts valve 34 to control the proportion of reservoir fluid that mixes with the recirculation fluid received from the pad to achieve the prescribed treatment pad temperature. For example, if the fluid injected to the treatment pad through quick-disconnect outlet 44 is at the prescribed temperature, controller 56 will adjust valve 34 so that no fluid is received from reservoir 24; in other words, pump 32, treatment pad 18, and air/water separator 36 form a closed-loop system (the fluid may flow in either direction). If the output fluid temperature drops, however, controller 56 will adjust valve 34 so that fluid from reservoir 24 mixes with recirculated water from air/water separator 36 in the proportion selected to achieve the desired output fluid temperature. Because the fluid volume in the fluid flow path defined by the pump, the treatment pad, and the air/water separator is substantially fixed, some recirculated fluid will be displaced and flow into reservoir 24 via overflow tube 50 to complete the heat exchange process.

To ensure uniform temperature distribution at the therapy site (or sites), a high flow rate is used to reduce the temperature gradient that develops across the treatment pad as a result of heat transfer at the treatment site. In some embodiments, the thermal therapy device includes multiple treatment pads coupled in series, which can be used, e.g., in the treatment of post bilateral surgery therapy. High flow rates are generally needed in these multi-pad embodiments to reduce the temperature differential between the upstream and downstream treatment pads. The flow rate can also be selected based on the anticipated heat load at the treatment site.

Figure 3:
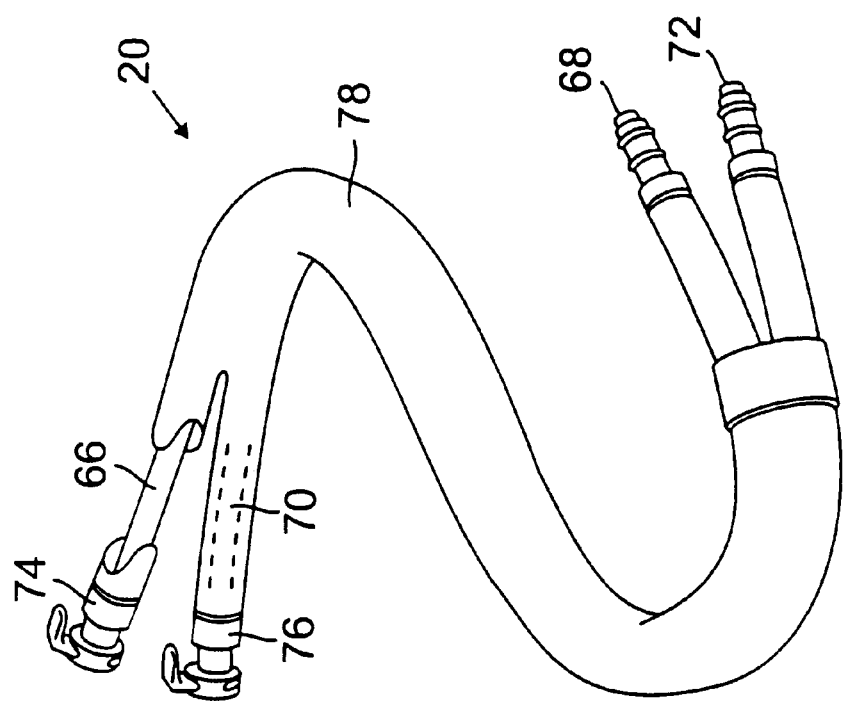
FIG. 3 is a diagrammatic view of insulated fluid supply and return lines a thermal therapy device of the invention.

Referring to FIG. 3, insulated supply and return assembly 20 includes a flexible fluid supply line 66 that connects to quick-disconnect outlet 44 via a mating quick-disconnect connector 68, and a flexible fluid return line 70 that connects to quick-disconnect return inlet 52. In the embodiment shown in FIG. 3, the supply and return line assembly 20 is attached to the treatment pad via quick-disconnect connectors 74, 76. The flexible supply and return lines 66, 70 are encased in thermal insulation 78 (e.g., polyurethane foam) that reduces ambient heat loads, makes the entire line assembly fluid tight, durable and flexible, and is more comfortable for the user to handle. The length of the supply and return line assembly is selected based at least in part on the size of the user and on the anticipated thermal therapy treatment.

Figure 4:
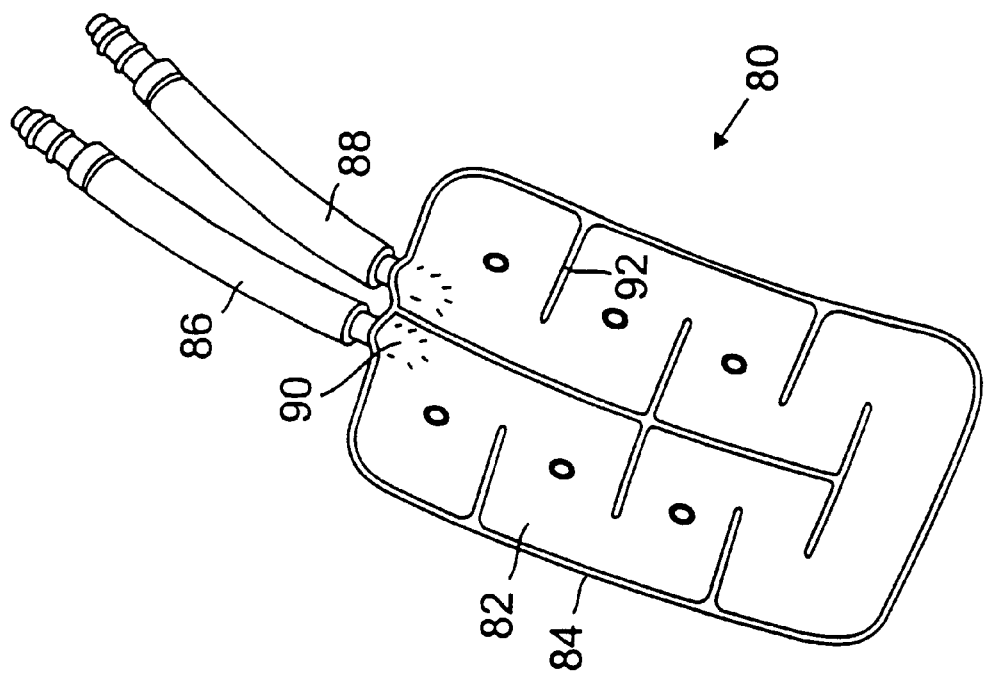
FIG. 4 is a diagrammatic view of a thermal therapy treatment pad for a device of the invention.

Various treatment pad shapes and sizes are contemplated depending on the selected treatment site (e.g., ankle, knee, elbow), with the object being to sufficiently cover the treatment site to achieve optimal therapy results. In the embodiment shown in FIG. 4, a treatment pad 80 is formed of two layers of flexible polymeric material 82 that are heat-welded or otherwise sealed together at the outer edge 84 of the pad. In this embodiment, supply and return lines 86, 88 are permanently attached to treatment pad 80 by a leak proof seal 90. Pad 80 also includes one or more internal seams 92 (or internal walls), which uniformly direct the flow of cooling fluid through the pad; the internal seams also control the expansion and contraction of the pad.

Referring to FIGS. 5 and 5A, treatment pad 80 is constructed to allow the pad to expand (FIG. 5) and to contract (FIG. 5A) in response to varying fluid pressures applied by the heat exchanger, and to ensure a uniform distribution of circulating fluid within the pad. To achieve tactile stimulation, pump 32 is turned off and on at preprogrammed intervals to periodically allow the pressure in the treatment pad to be cycled between low and high values. Such a periodic pressure variation in the treatment pad provides tactile stimulation at the therapy site while achieving the desired therapy temperature. Controller 56 (FIG. 2) can be programmed to simultaneously provide the desired temperature profile and the desired tactile stimulation.

Figure 6:
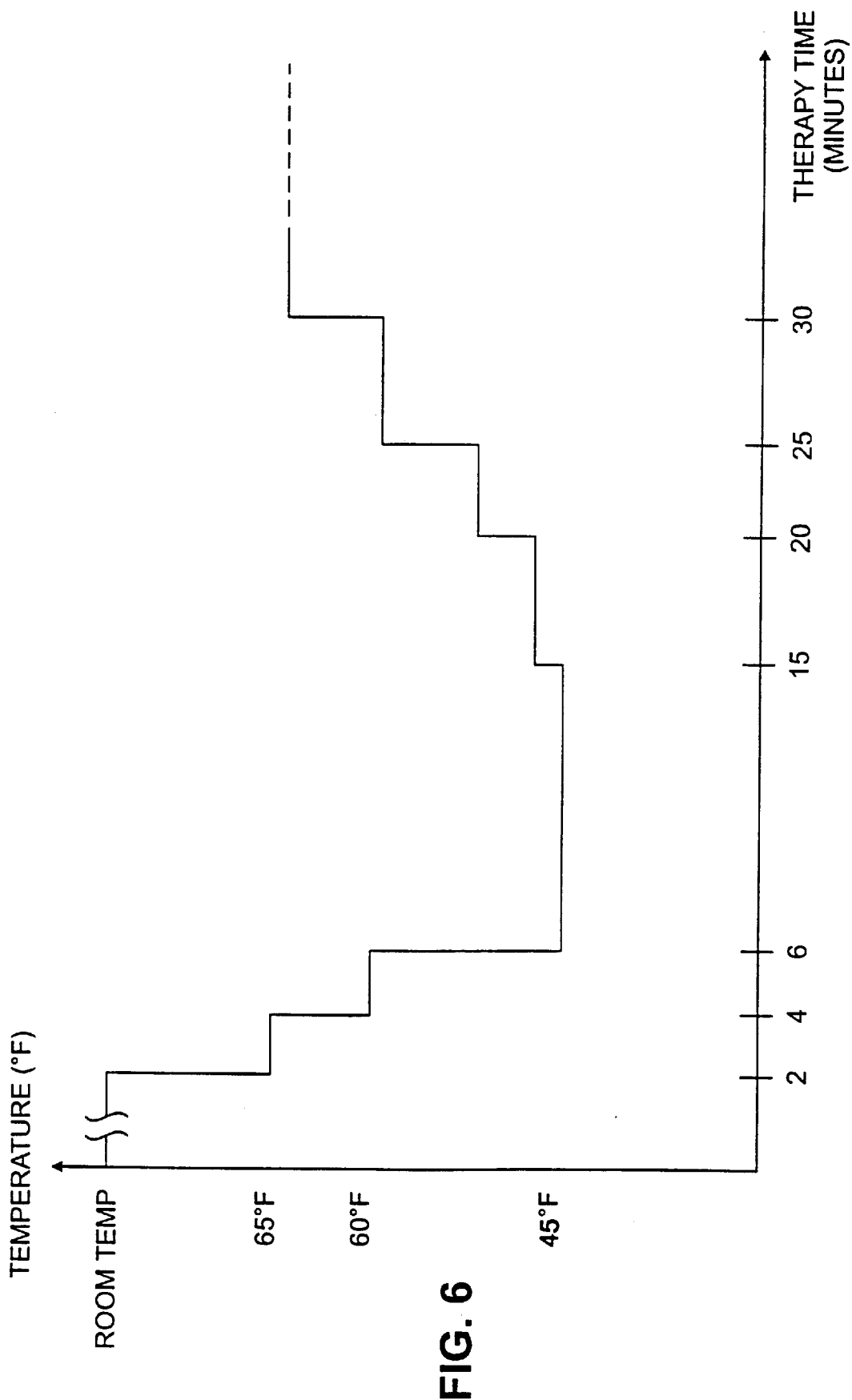
FIG. 6 is a therapy temperature time profile programmed into a therapy device controller.

Although a constant therapy temperature time profile may be programmed into controller 56, it is preferable to vary the temperature during treatment to avoid discomfort and permit long term thermal therapy without causing tissue damage. As shown in FIG. 6, a preferred cold therapy temperature time profile calls for a reduction in the applied therapy temperature from room temperature to a predetermined minimum temperature (e.g., 45° F.) during an initial treatment stage; during an intermediate stage the minimum therapy temperature is maintained for a fixed period (e.g., nine minutes); and during a final treatment stage the temperature is increased at regular intervals (e.g., every five minutes) until the treatment temperature is at about 65° F. The applied therapy temperature is maintained at 65° F. for the duration of the prescribed treatment period.

Other embodiments are within the scope of the claims.

For example, in one embodiment, the thermal therapy device uses two pumps, instead of the combination of a single pump and a single pole, double-throw valve, to achieve bi-directional flow, closed-loop temperature control and increased tactile stimulation. Such a dual-pump device implements closed-loop temperature control using analog control electronics in the form of a solid state thermostat with the therapy site temperature selected with a mechanically operated device, such as a potentiometer in conjunction with a temperature read-out device. Increased tactile stimulation for a dual-pump device could be achieved by engaging both pumps simultaneously, imposing momentary higher pressure on the pad with no net fluid flow.

Automatic Closed-Loop Heat Exchanger

Figure 7:
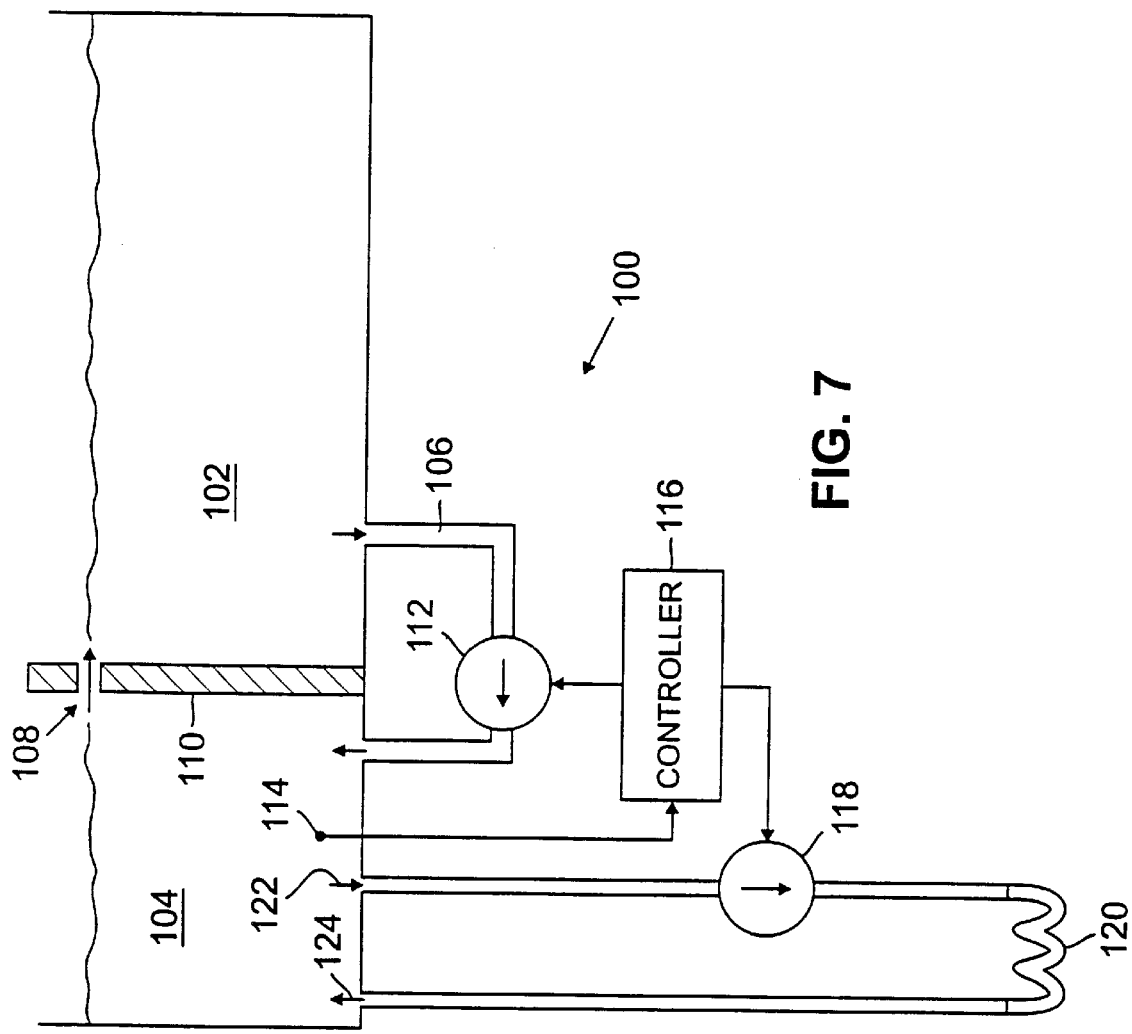
FIG. 7 is a schematic diagram of an alternative thermal therapy device.
Figure 2A:
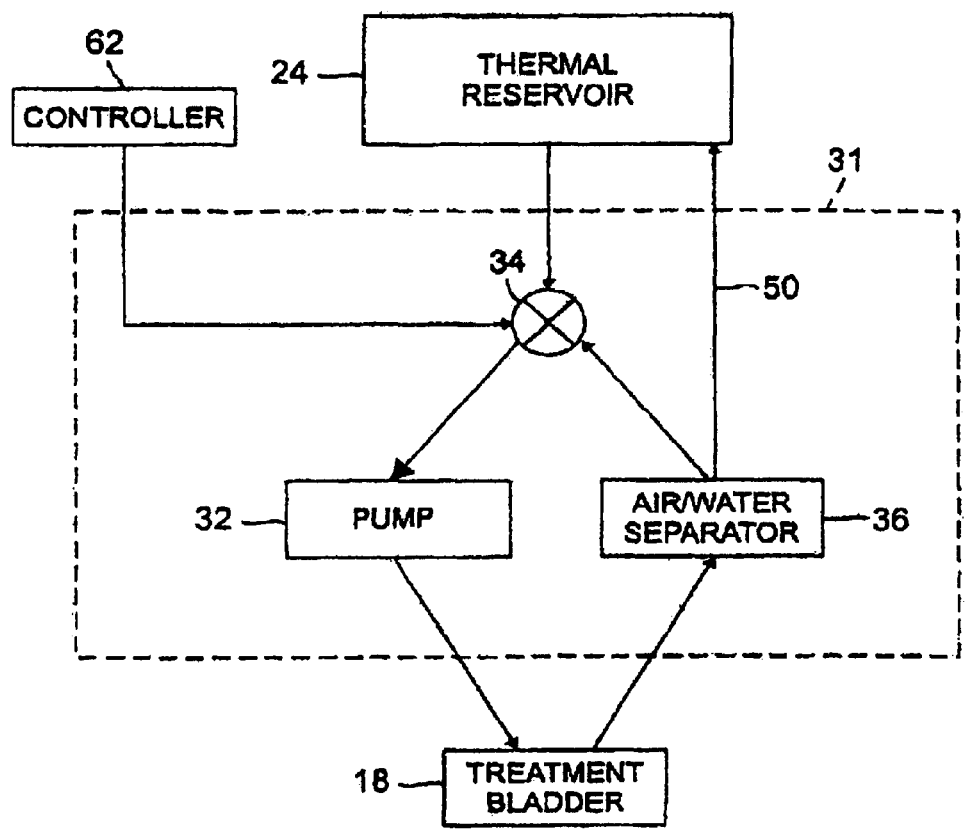

Referring to FIG. 7, a thermal therapy device 100 includes a primary reservoir 102 that is coupled to a secondary reservoir 104 by an active flow path 106 and by an overflow path 108; the primary and secondary reservoirs are separated by a thermal barrier 110. Active flow path 106 includes a dedicated constant pressure circulation pump 112. The temperature of the fluid in the secondary reservoir is monitored using a thermal sensor 114. A controller 116 adjusts the pump rate to maintain the temperature in the secondary reservoir at a desired temperature by controlling the fluid flow from the primary reservoir. Any excess fluid in the secondary reservoir is returned to the primary reservoir through overflow fluid path 108, completing the heat exchange circuit. A high speed circulation pump 118 controllably injects fluid from secondary reservoir 104 into a thermal therapy treatment pad 120.

The closed-loop electronic control allows the temperature of the secondary reservoir fluid to be maintained at a desired set-point value within about ±0.3° F. in a desired temperature range (e.g., 45° F. to 65° F., with the temperature of the primary reservoir fluid at about 35° F.) for practical thermal loads. When the secondary reservoir fluid temperature corresponds to the programmed temperature, the controller adjusts the pump speed so that the thermal transfer from the primary reservoir makes up for the thermal transfer at the treatment site through the treatment pad, which is represented by the difference in temperature between fluid 122 injected into the pad and fluid 124 returning from the pad. When the temperature profile programmed into controller 116 indicates that the therapy temperature is to be changed, the controller increases or decreases the speed of pump 112, depending on whether the applied temperature is to be increased or decreased. Because the fluid from the secondary reservoir is injected into the treatment pad at a high rate, the thermal load at the treatment site does not substantially affect the temperature of the fluid through the treatment pad and, consequently, the temperature differential across the treatment pad is maintained within about 2–3° F. of the programmed set-point value.

Reservoir 102 accommodates crushed ice, ice cubes and pre-formed freezable cold sources, such as, those commonly used in portable coolers. The reservoir is easily recharged with additional ice if needed during use, without requiring the person to remove the pad from the therapy site. For heat therapy, hot water can be introduced into the reservoir, or the reservoir fluid can be controllably heated using an immersion heater. Because ice water is used for the primary thermal reservoir, the thermal therapy device is highly cost-effective.

Manual Open-Loop Heat Exchanger

Referring to FIG. 8, a thermal therapy device 130 includes a primary thermal reservoir 132 and a secondary thermal reservoir 134. As in the embodiments described above, primary thermal reservoir 132 can accommodate a mixture of water and crushed ice or other cold source, or heated fluid. The mixing ratio of primary reservoir fluid 133 and recirculation fluid 135 from the secondary reservoir is adjusted by a manually-controlled valve 136. A high speed circulation pump 138 controls the flow of fluid into a thermal therapy treatment pad 140. Any excess fluid in the secondary reservoir is returned to the primary reservoir through overflow path 142, which completes the heat exchange circuit.

By adjusting valve 136 a user can empirically control the temperature of the secondary in an open-loop fashion. The water is mixed within the pump creating a near constant temperature within the circulation loop and the secondary reservoir. Preferably, valve 136 includes markings that indicate the correspondence between valve position and treatment temperature. For example, in one embodiment, valve 136 includes a marking that corresponds to a mixing ratio needed to provide a temperature of 45° F., which the user may apply to the treatment site for the initial period of treatment (e.g., ten to fifteen minutes). Valve 136 also includes a second marking that corresponds to a mixing ratio needed to provide a temperature of 65° F., which the user may apply to the treatment site indefinitely.

Still other embodiments are within the scope of the claims.

We claim:

1. A thermal therapy device for applying temperature-controlled therapy to a therapy site on a mammalian body, comprising:

a therapy pad for applying temperature-controlled therapy to the therapy site;

a recirculation fluid loop comprising a fluid channel defined by said therapy pad;

a thermal reservoir for containing fluid;

a fluid exchanger coupling said thermal reservoir with said recirculation fluid loop, said fluid exchanger being constructed to exchange an adjustable amount of fluid in said recirculation fluid loop with thermal reservoir fluid.

2. The therapy device of claim 1, further comprising a control mechanism coupled to said fluid exchanger for enabling adjustable control of the exchange of fluid in said recirculation fluid loop with thermal reservoir fluid to thereby control the temperature of the fluid circulating in said recirculation fluid loop.

3. The therapy device of claim 2, further comprising a pump for circulating fluid through said recirculation fluid loop, wherein said therapy pad includes a flexible surface and wherein said control mechanism is coupled to said pump for enabling adjustable control of fluid pressure in said therapy pad.

4. The therapy device of claim 3, wherein said control mechanism is adapted to vary pressure of recirculating fluid within said therapy pad in a manner to apply tactile stimulation to a therapy site by increasing and decreasing fluid pressure in said therapy pad.

5. The therapy device of claim 2, wherein said control mechanism comprises an alarm adapted to actuate whenever said thermal reservoir lacks thermal capacity to maintain a predetermined therapy temperature.

6. The therapy device of claim 1, wherein said recirculating fluid loop comprises a first temperature sensor for monitoring therapy temperature.

7. The therapy device of claim 6, further comprising control electronics coupled to said first temperature sensor, user-operated controls and a display for manual selection and visual confirmation of therapy temperature, said control electronics comprising an associated operating program and means for programming, storing and retrieving a therapy temperature-time profile for implementing therapy temperature control.

8. The device of claim 7, wherein said control electronics further comprises means for determining a time-varying therapy temperature specified in said therapy temperature-time profile in real time for implementing therapy temperature control.

9. The device of claim 8, wherein said control electronics further comprises means for comparing time-varying therapy temperature applied at said therapy site to a temperature specified in said therapy temperature-time profile in real time for implementing closed-loop therapy temperature control.

10. The therapy device of claim 7, wherein said control electronics further comprises an alarm for warning a user when said thermal reservoir lacks thermal capacity to maintain therapy temperature.

11. The therapy device of claim 10, wherein said alarm comprises a second temperature sensor connected to said control electronics for monitoring temperature in said recirculating fluid loop of fluid exiting said therapy pad, said first temperature sensor monitoring temperature in said recirculating fluid loop of fluid entering said therapy pad, said control electronics monitoring said first temperature sensor and said second temperature sensor and producing a signal when temperatures detected by said first temperature sensor and said second temperature sensor indicate that said thermal reservoir has insufficient thermal capacity to maintain a selected therapy temperature within a preset tolerance value.

12. The therapy device of claim 1 further comprising a second thermal reservoir.

13. The therapy device of claim 12, wherein said second thermal reservoir is constructed and arranged to function as an air/water separator.

14. The therapy device of claim 12 wherein said heat exchanger comprises a valve for selectively mixing fluid from said first thermal reservoir with fluid from said second thermal reservoir according to a prescribed mixing ratio and for introducing mixed fluid to said pump for circulation in said recirculating fluid loop.

15. The therapy device of claim 14 wherein said control mechanism comprises a knob for manually adjusting said valve to achieve the prescribed mixing ratio.

16. The therapy device of claim 12, wherein said fluid exchanger is adapted to inject a controllable amount of fluid from said first thermal reservoir into said second thermal reservoir.

17. The therapy device of claim 12, wherein said recirculation fluid loop is adapted to deliver fluid into, and to draw fluid from, said second thermal reservoir.

18. The therapy device of claim 12, wherein said fluid exchanger is adapted to supply fluid into said recirculation fluid loop from said first and second thermal reservoirs in an adjustable mixing ratio.

19. The therapy device of claim 18, wherein the fluid channel of said recirculation fluid loop is coupled between said second thermal reservoir and said fluid exchanger.

20. A thermal therapy device for applying temperature controlled therapy to a therapy site on a mammalian body, comprising:
   a therapy pad for applying a selected therapy temperature to the therapy site;
   a recirculation fluid loop comprising a fluid channel defined by said therapy pad;
   a first pump for circulating fluid through said recirculating fluid loop;
   a first thermal reservoir;
   a heat exchanger coupling said thermal reservoir with said recirculating fluid loop, said heat exchanger comprising a second thermal reservoir and a second pump for delivering fluid from said first thermal reservoir to said second thermal reservoir, and further comprising an overflow fluid path for returning excess fluid in said second thermal reservoir to said first thermal reservoir; and
   a control mechanism coupled to said heat exchanger for enabling adjustable control of therapy temperature.

21. The therapy device of claim 20 wherein said control mechanism selectively adjusts said second pump to achieve a prescribed fluid temperature in said second thermal reservoir.

22. A thermal therapy device for applying temperature controlled therapy to a therapy site on a mammalian body, comprising:
   a therapy pad for applying a selected therapy temperature to the therapy site;
   a recirculating fluid loop comprising a fluid channel defined by said therapy pad;
   a thermal reservoir; and
   a fluid exchanger coupling said thermal reservoir with said recirculating fluid loop, said heat exchanger being constructed and arranged to selectively mix fluid recirculating in said fluid loop with fluid from said thermal reservoir in an adjustable mixing ratio to achieve the selected therapy temperature at the therapy site.

23. The therapy device of claim 22 further comprising a pump for circulating fluid through said recirculating fluid loop.

24. The therapy device of claim 23 further comprising a control mechanism coupled to said fluid exchanger for enabling adjustable control of the mixing ratio to achieve the selected therapy temperature at the therapy site.

25. A thermal therapy device comprising:
   a reservoir for containing a fluid;
   a fluid line having an input for delivering fluid to a therapy pad and an output for receiving fluid from the therapy pad;
   a pump coupled to the fluid line for circulating fluid through the fluid line; and
   a fluid exchanger for exchanging a controlled amount of fluid in said fluid line with fluid from the reservoir to achieve a desired fluid temperature in the fluid line.

26. The thermal therapy device of claim 25 wherein the fluid exchanger comprises a diverter valve.

27. The therapy device of claim 26 wherein the diverter valve is manually-controllable.

28. The thermal therapy device of claim 25 wherein the fluid line comprises a second reservoir.

29. The thermal therapy device of claim 25 further comprising a therapy pad coupled to the input and the output of the fluid line.

30. The thermal therapy device of claim 25 wherein the fluid exchanger is adapted to displace a controlled amount of fluid out of the fluid line.

31. The thermal therapy device of claim 30 wherein the amount of fluid mixed into the fluid line from the reservoir is substantially equal to the amount of fluid displaced out of the fluid line.

32. The thermal therapy device of claim 21 wherein the fluid exchanger comprises a second pump.

33. A thermal therapy device comprising:
   a reservoir for containing a fluid;
   a fluid line having an input for delivering fluid to a therapy pad and an output for receiving fluid from the therapy pad;
   a pump coupled to the fluid line for circulating fluid through the fluid line; and a fluid exchanger for mixing a controlled amount of fluid from the reservoir into the fluid line to achieve a desired fluid temperature in the fluid line, the fluid exchanger comprising a second pump.

34. A thermal therapy device for applying temperature-controlled therapy to a therapy site on a mammalian body, comprising:
   a therapy pad for applying temperature-controlled therapy to the therapy site;
   a recirculation fluid loop comprising a fluid channel defined by the therapy pad and containing recirculation fluid;
   a thermal reservoir constructed to contain fluid;
   a fluid exchanger coupling the thermal reservoir with the recirculation fluid loop, the fluid exchanger being constructed to exchange an adjustable amount of recirculation fluid returning from the therapy pad with a substantially equal amount of thermal reservoir fluid and to mix the unexchanged recirculation fluid returning from the therapy pad with the substantially equal amount of thermal reservoir fluid, wherein the unexchanged recirculation fluid and the substantially equal amount of thermal reservoir fluid are delivered to the therapy pad.

35. The therapy device of claim 34, further comprising a control mechanism coupled to the fluid exchanger for enabling adjustable control of the exchange of recirculation fluid with thermal reservoir fluid to thereby control the temperature of the fluid circulating in the recirculation fluid loop.

36. The therapy device of claim 35, further comprising a pump for circulating fluid through the recirculation fluid loop.

37. A thermal therapy device for applying temperature-controlled therapy to a therapy site on a mammalian body, comprising:
   a therapy pad including recirculation fluid for applying temperature-controlled therapy to the therapy site;

a pump;

a diverter valve; and a thermal reservoir constructed to contain fluid coupled to the pump;

wherein fluid flows through a recirculation loop comprising the pump, the therapy pad, and the diverter valve and containing recirculation fluid, the diverter valve diverting from the recirculation loop an adjustable amount of recirculation fluid returning from the therapy pad, and the pump draws from the thermal reservoir and injects into the recirculation loop an amount of thermal reservoir fluid substantially equal to the amount of recirculation fluid diverted by the diverter valve, wherein non-diverted recirculation fluid returning from the therapy pad mixes with fluid drawn from the thermal reservoir and is delivered to the therapy pad.

38. The therapy device of claim 37, wherein the diverter valve is further coupled to the thermal reservoir for delivering recirculation fluid diverted from the recirculation loop into the thermal reservoir.

* * * * *

(12) EX PARTE REEXAMINATION CERTIFICATE (8499th)
United States Patent
Kolen et al.

(10) Number: US 5,980,561 C1
(45) Certificate Issued: Aug. 30, 2011

(54) APPLYING THERMAL THERAPY TO LIVING TISSUE

(75) Inventors: Paul T. Kolen, Encinitas, CA (US);
Thomas D. Ford, San Diego, CA (US)

(73) Assignee: Credit Suisse, New York, NY (US)

Reexamination Request:
No. 90/011,076, Jun. 30, 2010

Reexamination Certificate for:
Patent No.: 5,980,561
Issued: Nov. 9, 1999
Appl. No.: 08/860,307
Filed: Dec. 31, 1997

(22) PCT Filed: Mar. 1, 1995
(86) PCT No.: PCT/US96/02824
§ 371 (c)(1),
(2), (4) Date: Dec. 31, 1997
(87) PCT Pub. No.: WO96/26693
PCT Pub. Date: Sep. 6, 1996

Related U.S. Application Data

(63) Continuation-in-part of application No. 08/450,641, filed on May 25, 1995, now Pat. No. 5,865,841.

(51) Int. Cl.
*A61F 7/00* (2006.01)

(52) U.S. Cl. .................................... 607/104; 607/114
(58) Field of Classification Search ...................... None
See application file for complete search history.

(56) References Cited

U.S. PATENT DOCUMENTS

| | | | |
|---|---|---|---|
| 3,316,732 A | 5/1967 | Burton | |
| 3,744,555 A | 7/1973 | Fletcher et al. | |
| 4,470,429 A | 9/1984 | Johnson | |
| 4,844,072 A | 7/1989 | French et al. | |
| 5,033,136 A | 7/1991 | Elkins | |
| 5,476,489 A | 12/1995 | Koewler | |
| 6,551,347 B1 | 4/2003 | Elkins | |

*Primary Examiner* — Beverly M. Flanagan

(57) ABSTRACT

A thermal therapy device for applying temperature controlled therapy to a therapy site on a mammalian body, comprising: a therapy pad for applying a selected therapy temperature to the therapy site; a recirculating fluid loop comprising a fluid channel defined by the therapy pad; a pump for circulating fluid through the recirculating fluid loop; a thermal reservoir; a heat exchanger coupling the thermal reservoir with the recirculating fluid loop; and a control mechanism coupled to the heat exchanger for enabling adjustable control of therapy temperature. The heat exchanger selectively mixes fluid recirculating in the fluid loop with fluid from the thermal reservoir in an adjustable mixing ratio to achieve the selected therapy temperature at the therapy site.

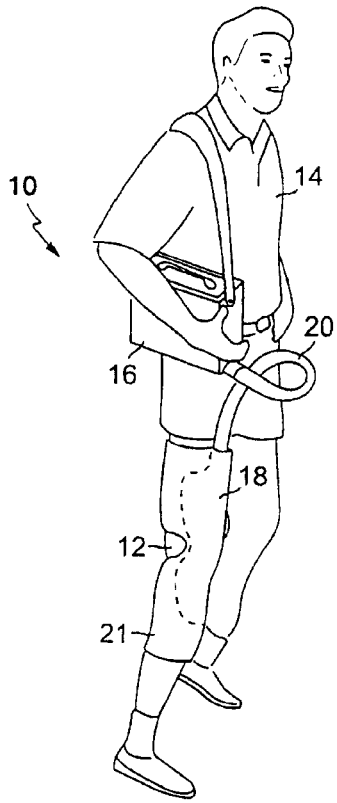

AMENDED SHEET

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

THE DRAWINGS FIGURE(S) HAVE BEEN CHANGED AS FOLLOWS:

FIG. 2A Changed Direction of Arrow Between Elements 32 and 34.

AS A RESULT OF REEXAMINATION, IT HAS BEEN DETERMINED THAT:

The patentability of claims 1-13, 16-21 and 25-38 is confirmed.

Claims 14 and 22 are determined to be patentable as amended.

Claims 15, 23 and 24, dependent on an amended claim, are determined to be patentable.

New claims 39-84 are added and determined to be patentable.

14. The therapy device of claim 12 wherein said [heat] *fluid* exchanger comprises a valve for selectively mixing fluid from said first thermal reservoir with fluid from said second thermal reservoir according to a prescribed mixing ratio and for introducing mixed fluid to said pump for circulation in said recirculating fluid loop.

22. A thermal therapy device for applying temperature controlled therapy to a therapy site on a mammalian body, comprising:
- a therapy pad for applying a selected therapy temperature to the therapy site;
- a recirculating fluid loop comprising a fluid channel defined by said therapy pad;
- a thermal reservoir; and
- a fluid exchanger coupling said thermal reservoir with said recirculating fluid loop, said [heat] *fluid* exchanger being constructed and arranged to selectively mix fluid recirculating in said fluid loop with fluid from said thermal reservoir in an adjustable mixing ratio to achieve the selected therapy temperature at the therapy site.

*39. The device of claim 25, where the fluid line is tubing that permits fluid to flow there-through.*

*40. The device of claim 39, wherein the fluid line includes tubing that by-passes the reservoir, allowing fluid to flow through the tubing to the fluid exchanger without passing through the reservoir.*

*41. The device of claim 25, where the fluid exchanger is disposed within the reservoir.*

*42. The device of claim 25, where fluid flowing from the output mixes with the reservoir fluid without passing through the reservoir.*

*43. The device of claim 29, wherein the therapy pad is disposed within a wrap that is shaped to hold the pad in place around a person's knee.*

*44. The device of claim 43, wherein the wrap includes a strap to allow the pad to be adjustably fitted to the knee.*

*45. A thermal therapy device for treating an orthopedic injury in a patient, comprising:*
- *a reservoir for containing a fluid;*
- *a therapy pad configured to wrap about the patient's limb;*
- *a fluid line having input tubing that delivers fluid to the therapy pad and output tubing that receives fluid exiting the therapy pad;*
- *a pump coupled to the fluid line that circulates fluid through the fluid line;*
- *a microprocessor controller that processes a first temperature measurement of fluid delivered to or exiting the pad; and*
- *a fluid exchanger in communication with the controller, wherein the fluid exchanger mixes a controlled amount of fluid in the output tubing with fluid from the reservoir, based on the first temperature measurement, to achieve a desired fluid temperature in the input tubing.*

*46. The device of claim 45, wherein the controller adjusts the flow rate of fluid in the input tubing based on an anticipated heat load at the patient's treatment site.*

*47. The device of claim 45, wherein the controller is configured to turn the pump on and off.*

*48. The device of claim 45, comprising a first thermister in the input fluid tubing, a second thermister in the output tubing, and wherein the microprocessor compares readings from the first and second thermisters and determines from those readings if the reservoir has lost a cooling capacity.*

*49. The device of claim 45, wherein the reservoir has first and second portions, the first portion having ice and water and the second portion being partially shielded from the ice in the first portion by a wall.*

*50. The device of claim 49, comprising an opening in the reservoir that permits fluid to flow from the first to the second portion.*

*51. The device of claim 45, wherein the fluid exchanger is the second portion and receives the controlled amount of fluid exiting the pad for mixing with fluid from the thermal reservoir.*

*52. The device of claim 45, where the reservoir has a housing and inner walls and the fluid exchanger is located outside the walls.*

*53. The device of claim 52, wherein the fluid exchanger includes a separator and valve, and the fluid line output connects the pad to the separator at a location outside the walls of the reservoir.*

*54. The device of claim 45, wherein the reservoir includes a chamber that is charged with ice and water and a lid that opens and closes to permit recharging of the chamber with ice.*

*55. The device of claim 45, comprisisng a display that allows a user to adjust and visually confirm the temperature of fluid entering the pad.*

*56. The device of claim 45, wherein the therapy pad includes a strap that attaches the pad to the patient's leg.*

*57. A thermal therapy device for treating a patient limb, comprising:*
- *a reservoir for containing a fluid;*
- *a therapy pad configured to wrap about the patient's limb;*
- *a fluid line having input tubing that delivers fluid to the therapy pad and output tubing that receives fluid exiting the therapy pad;*
- *a pump coupled to the fluid line that circulates fluid through the fluid line;*
- *a microprocessor controller that processes a first temperature measurement of fluid flowing within the fluid line;*
- *a fluid exchanger coupled to the reservoir and controller; and* by-pass tubing coupling the fluid exchanger to the output tubing, wherein the fluid exchanger is adjustable, based on the first temperature measurement, so as to receive a controlled amount of fluid from the pad via the by-pass tubing without passing that fluid through a reservoir.

58. The device of claim 57, wherein the reservoir includes a chamber that is charged with ice and water and a lid that opens and closes to permit recharging of the chamber with ice.

59. The device of claim 57, wherein the controller adjusts the flow rate of fluid in the input tubing based on an anticipated heat load at the treatment site.

60. The device of claim 57, wherein the fluid line comprises a path defined by the pump, the treatment pad, and an air/water separator.

61. The device of claim 60, wherein the path has a substantially fixed volume.

62. The device of claim 60, comprising an overflow tube through which fluid returning from the pad may be displaced into the reservoir.

63. A thermal therapy device comprising:
  a reservoir for containing reservoir fluid, the reservoir comprising a first portion containing ice mixed with the reservoir fluid, and a second portion that shares at least one wall with the first portion and is partially shielded from the first portion;
  a fluid line coupled to the reservoir and comprising input tubing for delivering fluid to a therapy pad and output tubing for receiving fluid from the therapy pad;
  a first pump coupled to the fluid line for circulating fluid through the fluid line; and
  a fluid exchanger comprising the second portion of the reservoir, and wherein fluid from the output tubing controllably mixes with reservoir fluid within the second portion to achieve a desired temperature of fluid flowing in the input tubing.

64. The device of claim 63, comprising a therapy pad.

65. The device of claim 64, wherein the therapy pad is a wrap that fits around a patient's limb.

66. The device of claim 65, wherein the wrap includes a strap for securing to the limb.

67. The device of claim 63, wherein the at least one wall protrudes into the reservoir.

68. The device of claim 63, wherein the at least one wall is disposed between the first and second portions of the reservoir.

69. The device of claim 63, wherein the at least one wall is disposed next to an opening that permits fluid to flow from the second portion to the first portion.

70. The device of claim 69, where the opening is an overflow path disposed above the at least one wall.

71. The device of claim 63, wherein the first and second portions share three walls.

72. The device of claim 63, wherein the second portion contains at least three walls and water within the three walls has a temperature that is adjustable by varying the flow rate of fluid into the second portion.

73. The device of claim 63, wherein a first portion of fluid returning from the pad passes into an ice and water mixture within the reservoir, and a second portion of fluid returning from the pad mixes with fluid from the ice and water mixture and recirculates to the pad.

74. The device of claim 73, wherein the rate of mixing of the second portion of fluid returning from the pad mixes with fluid from the ice and water mixture at a variable flow rate.

75. The device of claim 63, wherein the fluid exchanger includes a valve.

76. The device of claim 75, wherein the valve receives fluid tubing from the first portion and the second portion, the valve forming a mixing receptacle and having a valve output that provides temperature regulated fluid to the therapy pad.

77. The device of claim 63, wherein ice water from the first portion and fluid from the pad mix within the second portion while a pump draws the mixed fluid from the valve and directs it to the input tubing.

78. The device of claim 63, wherein the fluid exchanger includes a second pump that pumps fluid from the first portion into the second portion.

79. The device of claim 63, comprising a microprocessor controller that processes a first temperature measurement of fluid flowing within the fluid line.

80. The device of claim 63, wherein the controller adjusts the flow rate of fluid in the input tubing based on an anticipated heat load at the treatment site.

81. The device of claim 63, comprising an active flow path and overflow path, the active flow path having a constant pressure circulation pump.

82. A thermal therapy device comprising:
  a reservoir for containing a fluid;
  a fluid line having an input tube for delivering fluid to a therapy pad and an output tube that receives fluid from the therapy pad;
  a pump coupled to the fluid line for circulating fluid through the fluid line; and
  a fluid exchanger that exchanges a controlled amount of fluid in the output tube with fluid from the reservoir to achieve a desired fluid temperature in the input tube.

83. A thermal therapy device comprising:
  a reservoir for containing reservoir fluid, the reservoir comprising a first portion containing ice mixed with the reservoir fluid, and a second portion that shares at least one wall with the first portion and is partially shielded from the first portion;
  a fluid line coupled to the reservoir and comprising input tubing for delivering fluid to a therapy pad and output tubing for receiving fluid from the therapy pad;
  a first pump coupled to the fluid line for circulating fluid through the fluid line; and
  a fluid exchanger comprising the second portion of the reservoir, wherein a first portion of fluid returning from the pad passes by the at least one wall and into an ice and water mixture within the reservoir, and wherein within the second portion of the reservoir fluid from the ice and water mixture mixes with a second portion of fluid returning from the pad, forming a therapy fluid that recirculates to the pad.

84. A thermal therapy device for treating a patient's limb, comprising:
  a thermal reservoir for storing a fluid;
  a therapy pad configured to wrap about the patient's limb;
  a fluid line having input tubing that delivers fluid to a therapy pad and output tubing that receives fluid exiting the therapy pad;
  a pump coupled to the fluid line for circulates fluid through the fluid line;
  a microprocessor controller that processes a first temperature measurement of fluid delivered to or exiting the pad; and
  a fluid exchanger in communication with the controller, wherein the fluid exchanger mixes a controlled amount of fluid in the output tubing with fluid from the reservoir, based on the first temperature measurement, to achieve a desired fluid temperature in the input tubing.

* * * * *